US00PP36804P2

(12) United States Plant Patent
van Eijk

(10) Patent No.: US PP36,804 P2
(45) Date of Patent: Jul. 1, 2025

(54) ***ZANTEDESCHIA* PLANT NAMED 'DO21PW104'**

(50) Latin Name: *Zantedeschia authiopica*
Varietal Denomination: DO21PW104

(71) Applicant: EIJCO B.V., Nootdorp (NL)

(72) Inventor: Cornelis H. A. van Eijk, Nootdorp (NL)

(73) Assignee: EIJCO B.V., Nootdorp (NL)

( * ) Notice: Subject to any disclaimer, the term of this patent is extended or adjusted under 35 U.S.C. 154(b) by 0 days.

(21) Appl. No.: 19/004,282

(22) Filed: Dec. 28, 2024

(51) Int. Cl.
*A01H 6/10* (2018.01)
*A01H 5/02* (2018.01)

(52) U.S. Cl.
USPC ..... Plt./490
CPC ..... *A01H 6/10* (2018.05)

(58) Field of Classification Search
USPC ..... Plt./263.1, 490
See application file for complete search history.

(56) References Cited

U.S. PATENT DOCUMENTS

PP21,134 P2 * 6/2010 Klaver ..... A01H 5/02
Plt./490

* cited by examiner

*Primary Examiner* — Karen M Redden
(74) *Attorney, Agent, or Firm* — C. Anne Whealy

(57) ABSTRACT

A new and distinct cultivar of *Zantedeschia* plant named 'DO21PW104', characterized by its upright and broadly arching plant habit; high production of cut flowering stems; large white-colored spathes with light purple-colored lower surfaces and strong and erect scapes; good cut flower postproduction longevity; and relative tolerance to Soft Rot (*Erwinia carotovora*).

2 Drawing Sheets

Figure 1:
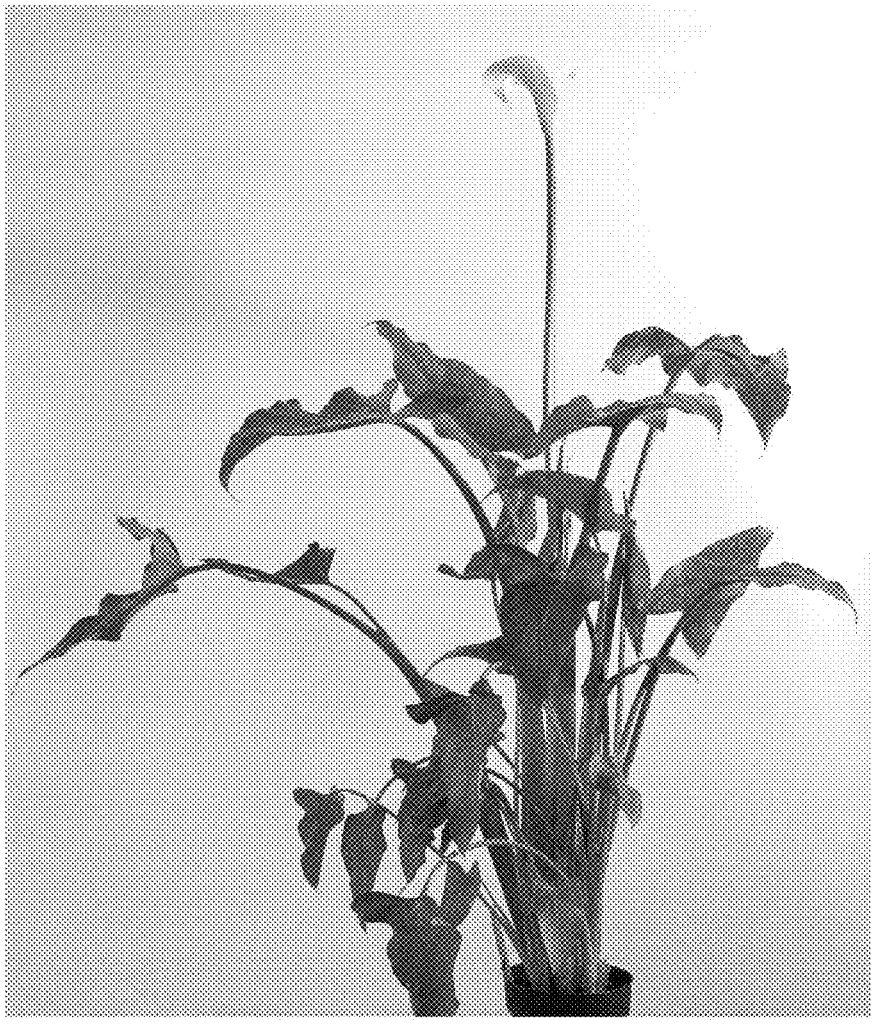

Botanical designation: *Zantedeschia aethiopica.*
Cultivar denomination: 'DO21PW104'.

PREVIOUSLY-FILED INTERNATIONAL APPLICATIONS

A European Community Plant Breeder's Rights application for the instant plant was filed by the Applicant/Assignee of the instant application, Eijco B. V. of Nootdorp, The Netherlands on Nov. 27, 2023, application number 2023/2527 and published on Feb. 15, 2024. Foreign priority is not claimed to this application.

A United Kingdom Plant Breeder's Rights application for the instant plant was filed by Mr. Paul Gooderham, the United Kingdom's Agent of the Applicant/Assignee, of the instant application, Eijco B. V. of Nootdorp, The Netherlands on Oct. 7, 2024, application number 616/5 and published on Nov. 1, 2024. Foreign priority is not claimed to this application.

BACKGROUND OF THE INVENTION

The present invention relates to a new and distinct cultivar of *Zantedeschia* plant, typically grown as a cut flower, botanically known as *Zantedeschia aethiopica*, commonly referred to as Calla Lily and hereinafter referred to by the name 'DO21PW104'.

The new *Zantedeschia* plant is a product of a controlled breeding program conducted by the Inventor in Nootdorp, The Netherlands. The objective of the breeding program is to create new freely flowering *Zantedeschia* plants that have unique and attractive inflorescence coloration.

The new *Zantedeschia* plant originated from a cross-pollination in June 2015, in Nootdorp, The Netherlands of an unidentified proprietary selection of *Zantedeschia aethiopica*, not patented, as the female, or seed, parent with an unidentified proprietary selection of *Zantedeschia aethiopica*, not patented, as the male, or pollen, parent. The new *Zantedeschia* was discovered and selected by the Inventor as a single flowering plant within the progeny of the stated cross-pollination in a controlled greenhouse environment in Nootdorp, The Netherlands in May 2017.

Asexual reproduction of the new *Zantedeschia* plant by rhizomes and rhizome division in a controlled environment in Quelfes, Portugal since July 2020 has shown that the unique features of this new *Zantedeschia* plant are stable and reproduced true to type in successive generations of asexual reproduction.

SUMMARY OF THE INVENTION

Plants of the new *Zantedeschia* have not been observed under all possible combinations of environmental and cultural conditions. The phenotype may vary somewhat with variations in environment such as temperature and light intensity, without, however, any variance in genotype.

The following traits have been repeatedly observed and are determined to be the unique characteristics of 'DO21PW104'. These characteristics in combination distinguish 'DO21PW104' as a new and distinct cultivar of *Zantedeschia:*

1. Upright and broadly arching plant habit.
2. High production of cut flowering stems.
3. Large white-colored spathes with light purple-colored lower surfaces and strong and erect scapes.
4. Good cut flower postproduction longevity.
5. Relatively tolerant to Soft Rot (*Erwinia carotovora*).

Plants of the new *Zantedeschia* can be compared to the parent selections. Plants of the new *Zantedeschia* differ from plants of the female parent selection in growth habit as plants of the new *Zantedeschia* are more uniform than plants of the parent selections. In addition, plants of new *Zantedeschia* produce more flowering stems than plants of the parent selections.

Plants of the new *Zantedeschia* can also be compared to plants of *Zantedeschia aethiopica* 'Flamingo', disclosed in U.S. Plant Pat. No. 21,134. In side-by-side comparisons, plants of the new *Zantedeschia* differ from plants of 'Flamingo' in the following characteristics:

1. Flowering stems of plants of the new *Zantedeschia* are longer than flowering stems of plants of 'Flamingo'.
2. Plants of the new *Zantedeschia* produce more flowering stems per meter than plants of 'Flamingo'.
3. Plants of the new *Zantedeschia* have white-colored flowers with light purple-colored lower surfaces whereas plants of 'Flamingo' have pink-colored flowers.
4. Plants of the new *Zantedeschia* are more tolerant to root pathogens common to *Zantedeschia* plants than plants of 'Flamingo'.

BRIEF DESCRIPTION OF THE PHOTOGRAPHS

The accompanying photographs illustrate the overall appearance of the new *Zantedeschia* plant. These photographs show the colors as true as it is reasonably possible to obtain in colored reproductions of this type. Colors in the photographs may differ slightly from the color values cited in the detailed botanical description which accurately describe the colors of the new *Zantedeschia*.

The photograph on the first sheet (FIG. 1) is a side perspective view of a typical plant of 'DO21PW104' grown in a container.

Figure 2:
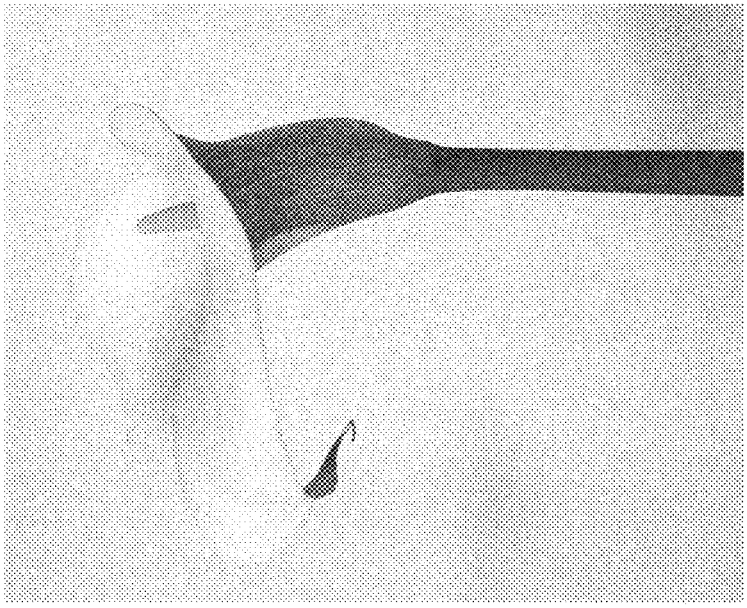

The photograph on the left side of the second sheet (FIG. 2) is a close-up view of a typical inflorescence of 'DO21PW104'.

Figure 3:
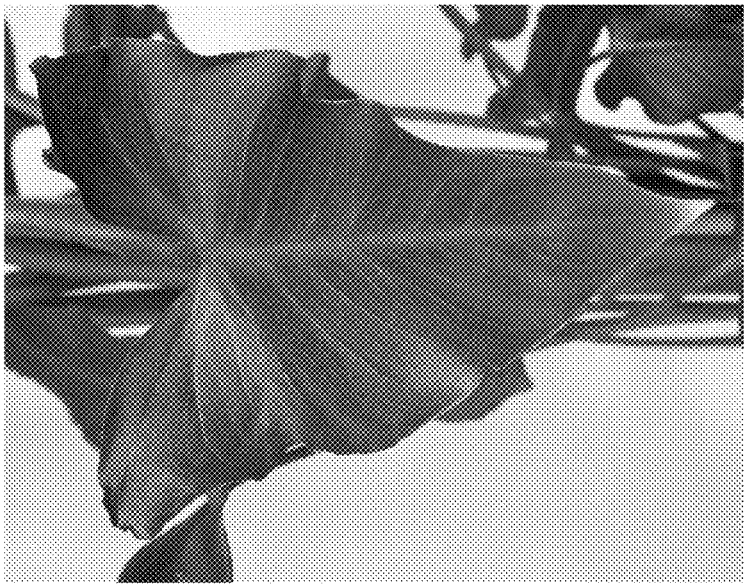

The photograph on the right side of the second sheet (FIG. 3) is a close-up view of typical leaves of 'DO21PW104'.

DETAILED BOTANICAL DESCRIPTION

The aforementioned photographs and following observations and measurements describe plants grown during the spring in 17-cm containers in a glass-covered greenhouse in Pijnacker, The Netherlands. Plants were grown under conditions and practices which approximate those generally used in commercial *Zantedeschia* cut flower production. During the production of the plants, day temperatures ranged from 15° C. to 25° C. and night temperatures ranged from 5° C. to 15° C. Plants were 50 weeks old when the photographs were taken and two years old when the detailed description was taken. In the following description, color references are made to The Royal Horticultural Society Colour Chart, Sixth Edition, 2019 Reprint, except where general terms of ordinary dictionary significance are used.

Botanical classification: *Zantedeschia aethiopica* 'DO21PW104'.

Parentage:

*Female, or seed, parent*.—Unidentified proprietary selection of *Zantedeschia aethiopica*, not patented.

*Male, or pollen, parent*.—Unidentified proprietary selection of *Zantedeschia aethiopica*, not patented.

Propagation:

*Type*.—By rhizomes or by rhizome division.

*Time to initiate roots*.—Variable, typically about one week at temperatures about 12° C. to 15° C.

*Time to produce a rooted young plant*.—Variable, typically about two months at temperatures about 12° C. to 19° C.

*Root description*.—Medium in thickness, fleshy; typically white in color; actual color of the roots is dependent on substrate composition, water quality, fertilizer, substrate temperature and age of roots.

*Rooting habit*.—Moderately freely branching; medium density.

Plant description:

*Plant habit*.—Upright and broadly arching plant habit; in outline, broad inverted triangle.

*Growth habit*.—Basally clumping; moderately vigorous to vigorous growth habit and moderate growth rate; about two flowering stems develop per plant.

*Plant height, from soil level to top of leaf plane*.—About 47.8 cm.

*Plant height, from soil level to top of inflorescences*.—About 76.8 cm.

*Plant diameter or spread*.—About 57.8 cm.

*Leaf description*.—Arrangement: Alternate, basal; simple. Length: About 24.1 cm. Width: About 11.8 cm. Shape: Sagittate. Apex: Narrowly acute with mucronate tip. Base: Sagittate. Margin: Entire; moderately and coarsely undulate. Texture and luster, upper and lower surfaces: Smooth, glabrous; slightly leathery; moderately glossy. Venation pattern: Pinnate. Color: Developing leaves, upper surface: Close to a blend of 137B and 143A. Developing leaves, lower surface: Close to 144A. Fully expanded leaves, upper surface: Close to 137B; venation, close to 144A. Fully expanded leaves, lower surface: Close to a blend of 143B and 144A; venation, close to N144C. Petioles: Length: About 43.8 cm. Diameter, distally: About 6 mm by 7 mm. Diameter, proximally: About 1.2 cm by 1.4 cm. Texture and luster, upper and lower surfaces: Smooth, glabrous; slightly glossy. Color, upper and lower surfaces: Close to 144A. Wing length: About 23.2 cm. Wing diameter: About 9 mm. Wing color: Close to 145D; venation, close to 144A and 144B.

Inflorescence description:

*Inflorescence arrangement*.—Spathes with spadices positioned within to above the foliar plane on strong and erect scapes; spathes, cup-shaped and revolute; spadices, cylindrical and tapering towards the apex.

*Inflorescence diameter*.—About 9.4 cm by 9.6 cm.

*Inflorescence depth*.—About 10.7 cm.

*Fragrance*.—None detected.

*Flowering season*.—In The Netherlands, flowering is continuous from spring into autumn; plants begin flowering about four to five months after planting rooted young plants.

*Quantity of inflorescences per plant*.—During the flowering season, typically about three inflorescences develop per plant.

*Inflorescence longevity*.—Depending on temperatures, inflorescences last about two weeks; inflorescences persistent.

*Spathe*.—Length: About 16.8 cm. Width: About 10.5 cm. Shape: Broadly ovate; cup-shaped. Apex:

Broadly acute with an elongated mucronate tip. Base: Cordate; lobes moderately imbricate. Margin: Entire; revolute; slightly and coarsely undulate. Texture and luster, upper and lower surfaces: Smooth, glabrous; matte. Aspect: About 110° from peduncle axis. Color: When developing, upper surface: Close to 157B and 157C; towards the apex and at the apex, close to 144B. When developing, lower surface: Close to 186B and 186C; towards the base and at the base, close to 144C and N144D; towards the apex and at the apex, close to 144B. Fully developed, upper surface: Close to NN155C fading towards the base to close to 157D; towards the apex and at the apex, close to 148A. Fully developed, lower surface: Close to 76B and NN155D; towards the base and at the base, close to NN144C; towards the apex and at the apex, close to 148A.

*Spadix*.—Length: About 5.8 cm. Diameter: About 8 mm. Shape: Cylindrical, tapering towards the apex; apex, obtuse; base, obtuse; cross-section, rounded. Aspect: About 12.5° from the peduncle axis. Color: Immature: Close to 10A and 11A. Mature: Close to 17A. Flowers, female: Arrangement and quantity: Positioned on the lower 20% of the spadix; about 75 per spadix. Shape: Rounded, flat. Height: About 1 mm. Diameter: About 1 mm. Stigma color: Close to 164B. Ovary color: Close to 194D. Flowers, male: Arrangement and quantity: Positioned on the upper 80% of the spadix; about 1,350 per spadix. Shape: Rounded, flat. Height: About 0.5 mm. Diameter: About 1 mm. Anther color: Close to 17A. Pollen amount: Abundant. Pollen color: Close to NN155A.

*Scape*.—Length: About 59.3 cm. Diameter, proximally: About 1.4 cm. Diameter, distally: About 7 mm. Strength: Strong. Aspect: Erect to about 20° from vertical. Color, proximally: Close to 147D; venation, close to 144A and 144B. Color, distally: Close to 144A; venation, close to 144A and 144B.

*Seed and fruit*.—To date, seed and fruit development has not been observed on plants of the new *Zantedeschia*.

Pathogen and pest tolerance: Plants of the new *Zantedeschia* have been observed to be relatively tolerant to Soft Rot (*Erwinia carotovora*). Plants of the new *Zantedeschia* have not been observed to be tolerant to pests and other pathogens common to *Zantedeschia* plants.

Temperature tolerance: Plants of the new *Zantedeschia* are suitable for USDA Hardiness Zones 9 through 12.

It is claimed:

1. A new and distinct *Zantedeschia* plant named 'DO21PW104' as herein illustrated and described.

* * * * *